(12) United States Patent
Morin et al.

(10) Patent No.: US 11,690,715 B2
(45) Date of Patent: Jul. 4, 2023

(54) COLLAPSIBLE LEAFLETS FOR PROSTHETIC HEART VALVES

(71) Applicant: St. Jude Medical, Cardiology Division, Inc., St. Paul, MN (US)

(72) Inventors: Kristen T. Morin, St. Paul, MN (US); Jay Reimer, Saint Paul, MN (US); Keith T. High, White Bear Lake, MN (US); Kristopher Henry Vietmeier, Monticello, MN (US); Tracee Eidenschink, Wayzata, MN (US); Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 96 days.

(21) Appl. No.: 17/211,976

(22) Filed: Mar. 25, 2021

(65) Prior Publication Data

US 2021/0315690 A1 Oct. 14, 2021

Related U.S. Application Data

(60) Provisional application No. 63/008,245, filed on Apr. 10, 2020.

(51) Int. Cl.
 *A61F 2/24* (2006.01)

(52) U.S. Cl.
 CPC ...... *A61F 2/2418* (2013.01); *A61F 2250/001* (2013.01)

(58) Field of Classification Search
 CPC ........ A61F 2/24; A61F 2/2418; A61F 2/2475; A61F 2/2409; A61F 2/246; A61F 2/2427
 See application file for complete search history.

(56) References Cited

U.S. PATENT DOCUMENTS

| | | | | |
|---|---|---|---|---|
| 4,265,694 A | * | 5/1981 | Boretos | A61F 2/2412 623/901 |
| 6,562,069 B2 | * | 5/2003 | Cai | A61F 2/2412 623/2.12 |
| 6,726,715 B2 | * | 4/2004 | Sutherland | A61F 2/2412 623/2.12 |
| 6,953,332 B1 | * | 10/2005 | Kurk | A61F 2/2412 264/303 |

(Continued)

FOREIGN PATENT DOCUMENTS

WO WO-2014004793 A2 * 1/2014 ............ A61F 2/2412

OTHER PUBLICATIONS

International Search Report including Written Opinion for PCT/US2021/024054 dated Jul. 7, 2021; 13 pages.

(Continued)

*Primary Examiner* — Seema Mathew
(74) *Attorney, Agent, or Firm* — Sleman & Lund LLP

(57) ABSTRACT

A prosthetic heart valve may include an expandable stent, a cuff attached to an annulus section of the stent, and a plurality of leaflets disposed within an interior region of the stent and attached to at least one of the cuff or the stent. The stent may have a plurality of cells connected to one another in a plurality of annular rows around the stent. The leaflets together may have a coapted position occluding the interior region of the stent and an open position in which the interior region is not occluded. Each leaflet may include a primary leaflet material, as well as features that reinforce specific regions of the leaflet.

15 Claims, 7 Drawing Sheets

(56) References Cited

U.S. PATENT DOCUMENTS

| | | | |
|---|---|---|---|
| 8,038,710 B2* | 10/2011 | Fearnot | A61F 2/2475 |
| | | | 623/2.12 |
| 10,143,551 B2 | 12/2018 | Braido et al. | |
| 10,195,023 B2* | 2/2019 | Wrobel | A61F 2/2418 |
| 10,426,609 B2* | 10/2019 | Edelman | A61F 2/2409 |
| 10,695,171 B2* | 6/2020 | Chuter | A61F 2/2412 |
| 2001/0049556 A1* | 12/2001 | Moe | A61F 2/2418 |
| | | | 623/2.14 |
| 2003/0055496 A1* | 3/2003 | Cai | A61F 2/2412 |
| | | | 623/2.19 |
| 2003/0078652 A1* | 4/2003 | Sutherland | A61F 2/2412 |
| | | | 623/2.12 |
| 2005/0075727 A1* | 4/2005 | Wheatley | A61F 2/2457 |
| | | | 623/902 |
| 2006/0276888 A1* | 12/2006 | Lee | A61F 2/2412 |
| | | | 623/2.14 |
| 2011/0190874 A1* | 8/2011 | Celermajer | A61F 2/2418 |
| | | | 623/1.26 |
| 2012/0116498 A1* | 5/2012 | Chuter | A61F 2/2412 |
| | | | 623/1.26 |
| 2013/0274874 A1* | 10/2013 | Hammer | A61F 2/2439 |
| | | | 623/2.12 |
| 2014/0005772 A1* | 1/2014 | Edelman | A61L 27/34 |
| | | | 29/890.12 |
| 2014/0163671 A1* | 6/2014 | Bruchman | A61L 27/56 |
| | | | 623/2.12 |
| 2015/0182332 A1* | 7/2015 | Edelman | B05B 7/0433 |
| | | | 623/2.17 |
| 2017/0086972 A1 | 3/2017 | Braido et al. | |
| 2017/0231758 A1* | 8/2017 | Bruchman | A61L 27/48 |
| | | | 156/331.7 |
| 2020/0323630 A1* | 10/2020 | Alkhatib | A61F 2/2418 |
| 2021/0322649 A1* | 10/2021 | Morin | A61L 27/54 |

OTHER PUBLICATIONS

Gale et al., U.S. Appl. No. 62/902,044, filed Sep. 18, 2019, titled "Collapsible Leaflets for Prosthetic Heart Valves".

* cited by examiner

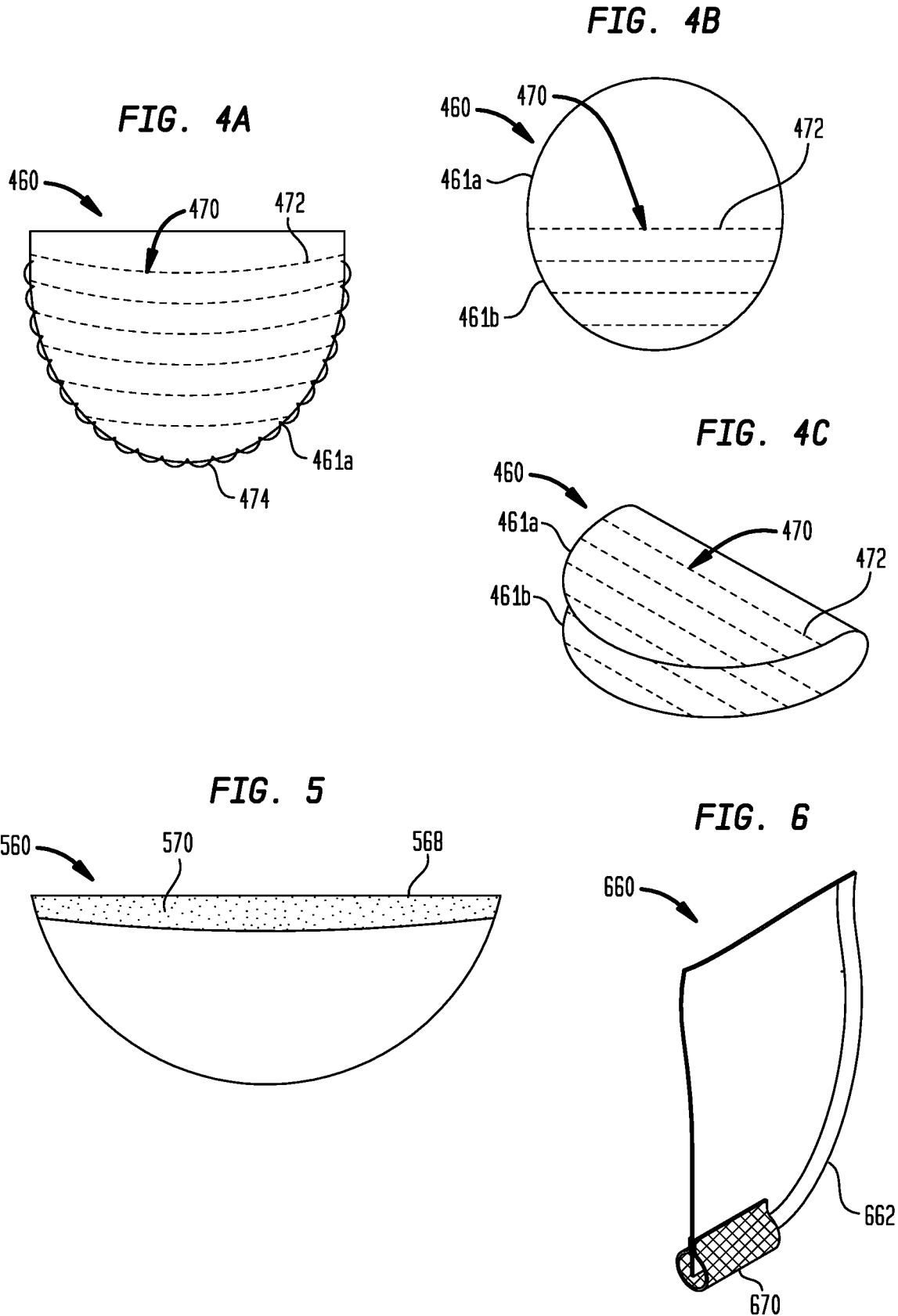

COLLAPSIBLE LEAFLETS FOR PROSTHETIC HEART VALVES

CROSS-REFERENCE TO RELATED APPLICATIONS

This application claims the benefit of the filing date of U.S. Provisional Patent Application No. 63/008,245 filed Apr. 10, 2020, the disclosure of which is hereby incorporated herein by reference.

BACKGROUND OF THE INVENTION

The present disclosure relates in general to heart valve replacement and, in particular, to prosthetic heart valves. More particularly, the present disclosure relates to leaflets for use in prosthetic heart valves.

Open-heart and transcatheter heart valve replacements are increasingly being performed in lower-risk patients. Such patients are typically younger than the higher-risk patient population that has traditionally received prosthetic heart valves, so they have a longer remaining life expectancy than traditional prosthetic heart valve recipients.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to collapsible prosthetic heart valves, conventional prosthetic heart valves suffer from some shortcomings. For example, in conventional collapsible prosthetic heart valves, the leaflets are typically made from biological tissue, such as porcine tissue. Over an extended patient lifespan, such biological leaflets may eventually erode or tear, creating a need for further surgical intervention or an additional valve replacement.

Biological leaflets may fail when excessively loaded or abraded. Biological leaflets have decent durability but may wear on the edges where they contact and coapt with one another and edges where they attach to the frame. Stresses in the tissue leaflets may limit valve durability by causing functional failures through tears or hole formation or acting as nodes for calcification initiation. Non-uniform or unbalanced leaflet coaptation may result in higher stresses in the leaflets, which may negatively impact valve durability.

There therefore is a need for further improvements to collapsible prosthetic heart valves. Among other advantages, the present invention may address one or more of these needs.

BRIEF SUMMARY OF THE INVENTION

The disclosure herein describes multiple embodiments of a prosthetic heart valve that include an expandable stent having an inflow end, an outflow end, an annulus section adjacent the inflow end, and a plurality of cells connected to one another in a plurality of annular rows around the stent; a cuff attached to the annulus section of the stent; a plurality of leaflets disposed within an interior region of the stent and attached to at least one of the cuff or the stent, the leaflets together having a coapted position occluding the interior region of the stent and an open position in which the interior region is not occluded, each leaflet including a primary leaflet material; and a support skeleton attached to the primary leaflet material of each leaflet, the support skeleton including a rigid reinforcing material having properties that are different from those of the primary leaflet material, such as a higher durometer than a durometer of the primary leaflet material.

Also described herein are multiple embodiments of a prosthetic heart valve that include an expandable stent having an inflow end, an outflow end, an annulus section adjacent the inflow end, and a plurality of cells connected to one another in a plurality of annular rows around the stent; a cuff attached to the annulus section of the stent; a plurality of leaflets disposed within an interior region of the stent and attached to at least one of the cuff or the stent, the leaflets together having a coapted position occluding the interior region of the stent and an open position in which the interior region is not occluded, each leaflet including a primary leaflet material; and a reinforcement attached to a surface of the primary leaflet material of each leaflet, the reinforcement including a material having properties that are different from those of the primary leaflet material, such as a higher durometer than a durometer of the primary leaflet material.

Further described herein are multiple embodiments of a prosthetic heart valve that include an expandable stent having an inflow end, an outflow end, an annulus section adjacent the inflow end, and a plurality of cells connected to one another in a plurality of annular rows around the stent; a cuff attached to the annulus section of the stent; a plurality of leaflets disposed within an interior region of the stent and attached to at least one of the cuff or the stent, the leaflets together having a coapted position occluding the interior region of the stent and an open position in which the interior region is not occluded, each leaflet including a primary leaflet material, and each leaflet having a thickness that varies from a belly of the leaflet to a free edge of the leaflet.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIG. 4A is a plan view of another embodiment of a leaflet suitable for use with the collapsible prosthetic heart valve of FIG. 1;

FIG. 4B is a plan view of the layers of the leaflet of FIG. 4A, shown in an unassembled condition;

FIG. 4C is a perspective view of the leaflet of FIG. 4A, shown before the leaflet layers are stitched to one another;

FIG. 5 is a plan view of another embodiment of a leaflet suitable for use with the collapsible prosthetic heart valve of FIG. 1;

FIG. 6 is a perspective view of a portion of another embodiment of a leaflet suitable for use with the collapsible prosthetic heart valve of FIG. 1;

DETAILED DESCRIPTION

As used herein in connection with a prosthetic heart valve, the term "inflow end" refers to the end of the heart valve through which blood enters when the heart valve is functioning as intended, and the term "outflow end" refers to the end of the heart valve through which blood exits when the heart valve is functioning as intended. As used herein in connection with a prosthetic heart valve, the term "proximal" refers to the inflow end of the heart valve or to elements of the heart valve that are relatively close to the inflow end, and the term "distal" refers to the outflow end of the heart valve or to elements of the heart valve that are relatively close to the outflow end. Also as used herein, the terms "generally," "substantially," "approximately," and "about" are intended to mean that slight deviations from absolute are included within the scope of the term so modified.

When used to indicate relative locations within the prosthetic heart valve, the terms "longitudinal" and "vertical" are to be taken as the direction of the axis extending between the inflow end and the outflow end of the stent of the heart valve, along the direction of intended blood flow; the term "flow direction" is to be taken as the direction from the inflow end to the outflow end of the stent of the heart valve; and the terms "above," "below," "high," and "low" are to be taken as relative to the inflow end of the stent. "Above" and "high" are to be understood as relatively farther from the inflow end of the stent in the direction of intended blood flow, and "below" and "low" are to be understood as relatively closer to the inflow end of the stent in the direction of intended blood flow. When used to indicate relative locations within the prosthetic heart valve, the term "circumferential" is to be taken as the direction of rotation about the longitudinal axis of the stent.

Figure 1:
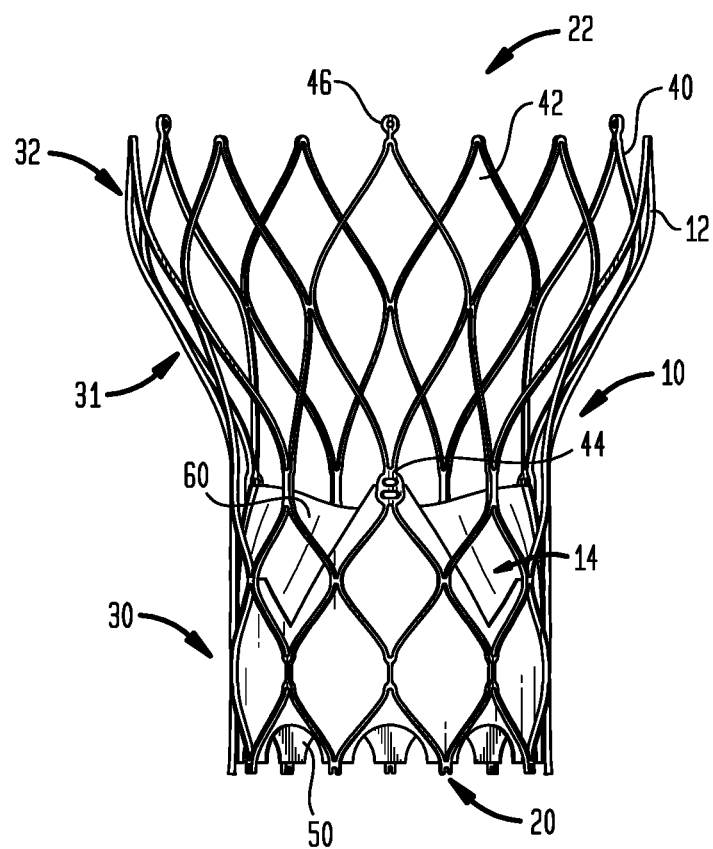
FIG. 1 is a side view of a conventional collapsible prosthetic heart valve.

FIG. 1 illustrates a collapsible and/or expandable stent-supported prosthetic heart valve 10 including a stent 12 and a valve assembly 14 as is known in the art. The prosthetic heart valve 10 is designed to replace a native heart valve of a patient, such as a native aortic valve, mitral valve, pulmonary valve, or tricuspid valve. It should be noted that while the example of FIG. 1 is described as a prosthetic aortic valve having a stent with a shape as illustrated, the valve could be a bicuspid valve, such as the mitral valve, and the stent could have different shapes, such as a flared or conical annulus section, a less-bulbous aortic section, and the like, and a differently shaped transition section between the annulus section and the aortic section. Any details of the structure and function of the prosthetic heart valve 10 that are not described herein may be found in U.S. Pat. No. 10,143,551, the entire disclosure of which is hereby incorporated by reference herein.

The stent 12 may be formed from biocompatible materials that are capable of self-expansion or expansion via a balloon, including, for example, shape memory alloys such as nitinol, or other suitable metals or polymers. The stent 12 extends from an inflow or annulus end 20 to an outflow or aortic end 22, and includes an annulus section 30 adjacent the inflow end, a transition section 31, and an aortic section 32 adjacent the outflow end. Each of the sections of stent 12 includes a plurality of struts 40 forming cells 42 connected to one another in one or more annular rows around the stent. For example, as shown in FIG. 1, the annulus section 30 may have two annular rows of complete cells 42 and the aortic section 32 and the transition section 31 may each have one or more annular rows of partial cells. The stent 12 may include one or more retaining elements 46 at the outflow end 22, the retaining elements being sized and shaped to cooperate with female retaining structures (not shown) provided within a transcatheter delivery device.

The prosthetic heart valve 10 includes the valve assembly 14 preferably positioned in the annulus section 30 of the stent 12 and secured to the stent. The valve assembly 14 includes a cuff 50 and a plurality of leaflets 60 that collectively function as a one-way valve by coapting with one another. As a prosthetic aortic valve, the prosthetic heart valve 10 has three leaflets 60. However, it will be appreciated that other prosthetic heart valves with which the leaflets of the present disclosure may be used may have a greater or lesser number of leaflets. Both the cuff 50 and the leaflets 60 may be wholly or partly formed of any suitable biological material (e.g., animal tissue such as pericardium tissue), fabric, or polymer that is impermeable to liquid such as, for example, polytetrafluoroethylene (PTFE), polyvinyl alcohol (PVA), ultra-high molecular weight polyethylene (UHMWPE), silicone, urethane, and the like. The cuff 50 and the leaflets 60 may be formed of the above materials or any of the additional materials described in the U.S. provisional patent application 62/902,044, the disclosure of which is hereby incorporated by reference herein.

The leaflets 60 may be attached along their belly portions to the cells 42 of the stent 12, with the commissure between adjacent leaflets being attached to commissure attachment features 44. As can be seen in FIG. 1, each commissure attachment feature 44 may lie at the intersection of four cells 42, two of the cells being adjacent one another in the same annular row, and the other two cells being in different annular rows and lying in end-to-end relationship. Each of the commissure attachment features 44 may include one or more eyelets that facilitate the suturing of the leaflet commissure to the stent 12.

The leaflets 60 are configured to move between an open position and a closed position in which the leaflets occlude a central opening of the valve assembly 14. The leaflets 60 are configured such that they are in the open position when the blood pressure at the annulus end 20 of the stent 12 is greater than the blood pressure at the aortic end 22, and are in the closed position when the blood pressure at the aortic end is greater than the blood pressure at the annulus end.

The prosthetic heart valve 10 may be used to replace a native aortic valve, a surgical heart valve, a heart valve that has undergone a surgical procedure, or any other valve that it is desired to replace. The prosthetic heart valve 10 may be delivered to the desired site (e.g., near or proximate a native valve annulus, or near or proximate an annuloplasty ring or other repair device) using any suitable delivery device.

During delivery, the prosthetic heart valve 10 may be disposed inside a transcatheter delivery device in a collapsed condition. The delivery device may be introduced into a patient using a transfemoral, transapical, transseptal, transradial, transsubclavian, transaortic or any other percutaneous approach. Once the delivery device has reached the target site, the user may deploy the prosthetic heart valve 10. Upon deployment, the prosthetic heart valve 10 expands so that the annulus section 30 is in secure engagement within the native valve annulus (or in engagement with an annuloplasty ring or other repair device). When the prosthetic heart valve 10 is properly positioned, it works as a one-way valve, allowing blood to flow in the flow direction, and preventing blood from flowing in the opposite direction.

Prosthetic valve leaflets bear stress when loaded during valve opening and coaptation. The leaflet variations that will be described below with reference to FIGS. 2A through 7B may redistribute or reduce the load borne by the primary material of these leaflets when the leaflets move back and forth between an open position and a coapted position.

Figure 2A:
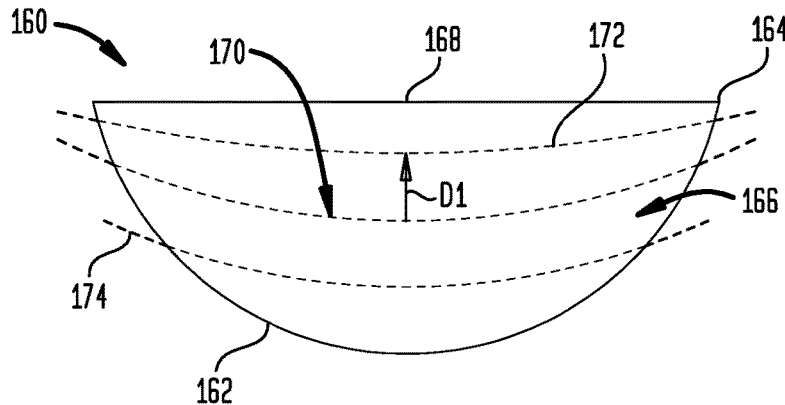
FIG. 2A is a plan view of one embodiment of a leaflet suitable for use with the collapsible prosthetic heart valve of FIG. 1.
Figure 2B:
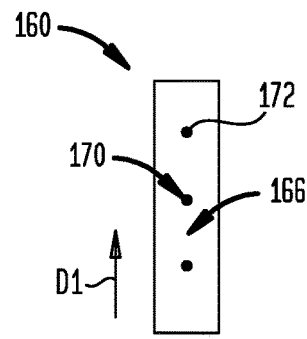
FIG. 2B is a side view of the leaflet of FIG. 2A.
Figure 2C:
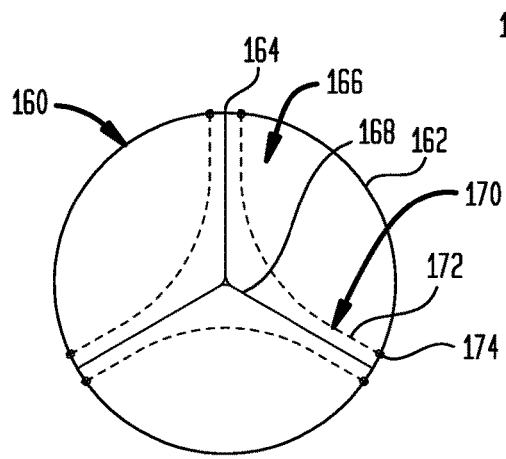
FIG. 2C is a plan view of three leaflets of FIG. 2A shown in a coapted position.

FIGS. 2A-2C illustrate a leaflet 160 according to an embodiment of the invention that may replace each of the leaflets 60 described above with reference to the prosthetic heart valve 10. The leaflet 160 may have the same function and shape as the leaflets 60. The leaflets 160 may be attached along their belly 162 to the cells 42 of the stent 12 of FIG. 1, with the commissure 164 between adjacent leaflets being attached to respective ones of the commissure attachment features 44. The leaflets 160 may be attached to the stent 12 and/or the cuff 50 using one or more sutures. The leaflets 160 may have a primary leaflet material that is derived from animal tissue (i.e., pericardium) or other compatible materials (such as fabric or polymers).

The leaflet 160 may have an internal skeleton 170 having ribs 172 that are made of a rigid or semi-rigid reinforcing material extending within the primary leaflet material through an interior volume 166 of the leaflet. The internal skeleton 170 may be formed of a biocompatible metal, such as nitinol, or a more flexible material, such as suture or other polymer. In some examples, the internal skeleton 170 may be formed of a braided wire material that is not made of metal, but that has rigidity similar to that of a metal wire. Other materials may be used, but it is desirable that such materials exhibit superelasticity or otherwise be able to bend substantially in order to effectively collapse the leaflets into a delivery device. It is desirable that the material of the internal skeleton 170 be elastic, to assist with valve opening, but soft enough (low durometer) so as not to inhibit leaflet closing. The ribs 172 may have a shape memory, such that the ribs are in a stress-free state when the leaflets 160 are closed, and the ribs are storing energy when the leaflets are in an open position so that they bias the leaflets towards a coapted position. In this way, the ribs 172 may actively assist leaflet coaptation. The internal skeleton 170 may include a rigid or semi-rigid reinforcing material having certain properties that are different from the properties of the primary leaflet material. For example, the reinforcing material may have a higher durometer than the durometer of the primary leaflet material, but not so high as to interfere with coaptation.

The ribs 172 of the internal skeleton 170 may lie within the interior volume 166 of the leaflet 160 and may be spaced apart from one another in a direction D1 that is parallel to an outer surface of the leaflet. Each rib 172 may have a roughened outer surface to reduce relative motion between the rib and the primary leaflet material, thereby promoting healing between the ribs and the primary leaflet material after implantation. Each of the ribs 172 may have a relatively small diameter compared to a thickness of the leaflet 160, so that structural integrity of the primary leaflet material is not compromised. For example, each rib 172 may have a diameter of between about 0.002 inches and about 0.020 inches.

When the ribs 172 of the internal skeleton 170 are embedded within the interior volume 166 of the leaflet 160, the material of the leaflet completely surrounds the ribs and holds them in place at fixed positions. However, in some embodiments the ribs 172 may be only partially embedded within the interior volume 166 of the leaflet 160, such as by being woven between the fibers of the leaflet fabric, or may be disposed on the outer surface of the leaflet. When the ribs 172 are woven between the fibers of the leaflet 160 so as to be exposed on both the top and bottom surfaces of the leaflet, the ribs may be held in place by heat sealing or welding together the interlaced fibers of the leaflet fabric immediately adjacent opposite sides of each rib. Heat sealing or welding these fibers together prevents the fibers from moving relative to one another, thereby trapping each rib 172 at a fixed position.

The ribs 172 may also be secured to the outer surface of the leaflet 160. One method of securing the ribs 172 to the leaflet 160 is to apply transverse strips of fabric (not shown) across each rib at spaced locations along the length of the rib. The strips of fabric may be heat sealed or welded to the leaflet 160 on opposite sides of the rib 172, holding the rib securely in place. The strips of fabric may be formed of the same material as forms the leaflet 160 or may be formed of a different material that can be easily heat sealed or welded to bond the strips to the leaflet. In an alternate arrangement, when the materials forming leaflet 160 and ribs 172 allow, the ribs may be directly heat sealed or welded to the leaflet without the use of ancillary strips of fabric.

Each of the ribs 172 may be bowed to a radius of curvature between that of a free edge 168 of the respective leaflet 160 and the belly 162. One or more of the ribs 172 may extend out of the interior volume 166 of the leaflet to form extensions 174. Each rib 172 may have an extension 174 extending out of the interior volume 166 at one end or both opposite ends of the rib. In one example, the extensions 174 may be attached to connectors (not shown) that could be coupled to the commissure attachment features 44.

One possible reinforcing layout of the internal skeleton 170 is depicted in FIGS. 2A-2C, although other orientations can be envisioned. In some instances, finite element analysis (FEA) could guide reinforcement layouts to target high-stress regions in the primary leaflet material. The layout of the internal skeleton 170 could also be oriented to incorporate material anisotropy (or alignment) in order to mimic native leaflet tissue.

Figure 2D:
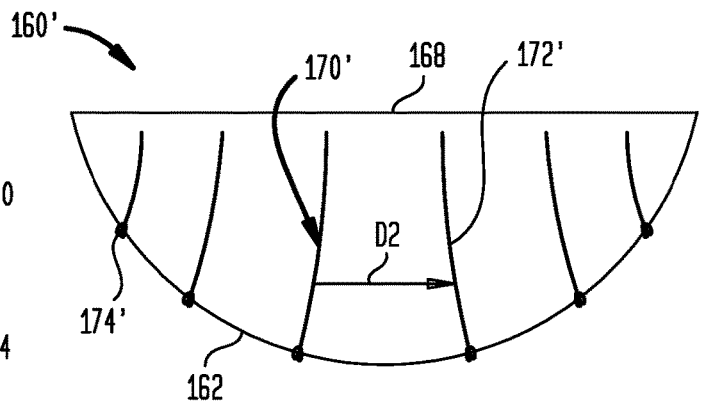
FIG. 2D is a plan view of a leaflet that is a variation of the leaflet of FIG. 2A.

FIG. 2D shows another possible reinforcing layout that is a variation of the embodiment of FIGS. 2A-2C, in which an internal skeleton 170' comprises a plurality of ribs 172' that are oriented in a direction that is generally perpendicular to the direction in which the ribs 172 of FIGS. 2A-2C are oriented. The ribs 172' extend from the belly 162 of the leaflet 160' towards the free edge 168, and may be attached to the leaflet 160' using any of the arrangements described above for attaching the ribs 172 to the leaflets 160. The ribs 172' extend generally perpendicular to the free edge 168 of the leaflet 160' and may be spaced apart from one another in a direction D2 that is parallel to an outer surface of the leaflet. Each rib 172' may be attached to the stent 12 and/or the cuff 50 at the belly 162 using a suture 174'. In one example, a rigid reinforcing material may be used for the ribs 172'. In this configuration, the leaflet 160' may have reduced bending while opening and closing compared to the leaflet 160. The internal skeleton 170' may include a rigid or semi-rigid reinforcing material having certain properties that are different from the properties of the primary leaflet material. In one example, the reinforcing material may have a higher durometer than a durometer of the primary leaflet material, but not so high as to interfere with coaptation.

Figure 2E:
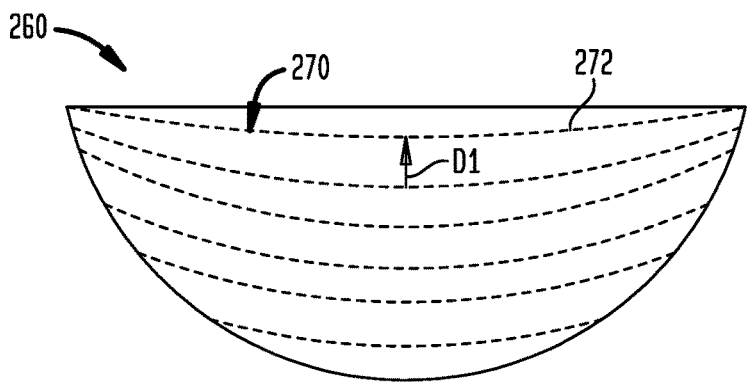
FIG. 2E is a plan view of a leaflet that is another variation of the leaflet of FIG. 2A.
Figure 2F:
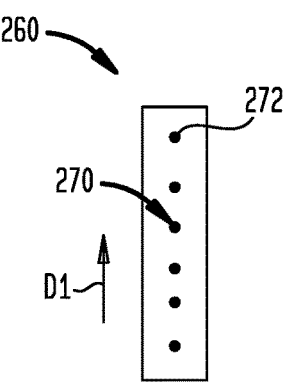
FIG. 2F is a side view of the leaflet of FIG. 2E.

FIGS. 2E and 2F show a leaflet 260, which is another variation of the leaflet 160, in which a solvent may be applied to the primary material of the leaflet, thereby creating reinforcing ribs 272 of the primary leaflet material that are more rigid than the surrounding primary leaflet material. The solvent may be applied to the primary leaflet material using various methods, including, but not limited to, injection, wicking, and soaking. After achieving adequate distribution of the solvent through the primary leaflet material, the solvent may be cured, for example, via drying or ultraviolet exposure.

The resulting internal skeleton 270 may have a rib structure similar to the internal skeleton 170 or 170', but the rib structure would be achieved by application of the solvent to form ribs 272 in place of the insertion of ribs 172 or 172' of a more rigid material into the primary leaflet material. In such a variation, the internal skeleton pattern achieved may have more ribs 272 that are spaced closer together than the ribs 172 or 172', thereby potentially evening out the stress experienced across the leaflet 260, but without compromising the structural integrity of the primary leaflet material. The ribs 272 may be spaced apart from one another in a direction D1 that is parallel to an outer surface of a respective one of the leaflets 260.

Figure 3A:
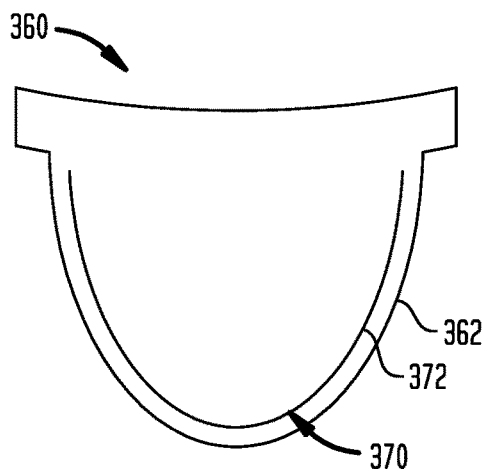
FIG. 3A is a plan view of another embodiment of a leaflet suitable for use with the collapsible prosthetic heart valve of FIG. 1.
Figure 3B:
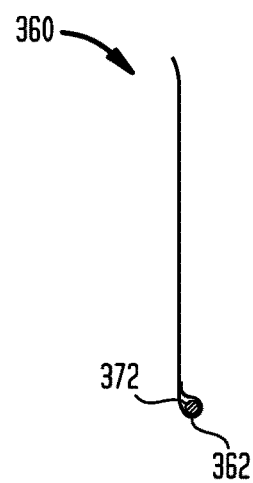
FIG. 3B is a side view of the leaflet of FIG. 3A.

FIGS. 3A and 3B illustrate a leaflet 360 according to an embodiment of the invention that may replace each of the leaflets 60 described above with reference to the prosthetic heart valve 10. The leaflet 360 is another variation of the leaflet 160 described above. The leaflet 360 may be the same as the leaflet 160, except that its internal skeleton 370 has a single rib 372 that extends along the belly 362, and the rib is secured to the primary leaflet material by having the edge of the belly wrapped around the rib as shown in FIG. 3B. The rib 372 may be made of a thin wire of nitinol, an MP35 nickel-based alloy, a spring metal, stainless steel, cobalt, or any of the other materials mentioned above with respect to the leaflet 160. The rib 372 may be heat set to introduce a bias to retain a desired shape with shape memory. To retain the rib 372 within the primary leaflet material, the primary leaflet material may be sealed to itself with heat sealing, an adhesive, sutures or another known sealing mechanism. The internal skeleton 370 may include a rigid reinforcing material having certain properties that are different from those of the primary leaflet material, such as a higher durometer than a durometer of the primary leaflet material, but not so high as to interfere with coaptation.

The rib 372 may assist the primary leaflet material in keeping a desired shape, which may shorten the timing of coaptation of the leaflets 360, and improve the consistency of coaptation, robustness of the leaflets to wear, and balance of coaptation (i.e., all three leaflets coapting at the same time). This latter feature may prevent one of the leaflets from experiencing wear faster than the other leaflets.

Figure 3C:
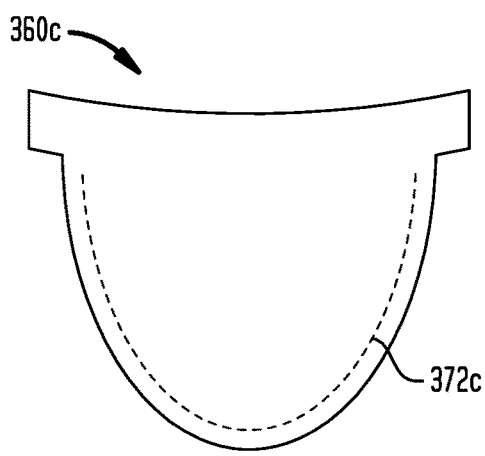
FIGS. 3C, 3D, and 3E are plan views of leaflets that are variations of the leaflet of FIG. 3A.

The leaflet 360c shown in FIG. 3C is similar to the leaflet 360, except that the leaflet 360c includes a single rib 372c that is threaded through the primary leaflet material in a manner similar to a suture, so it is not necessary to have the edge of the belly wrapped around the rib as shown in FIG. 3B. The rib 372c may be held securely in place on the leaflet 360c by heat sealing or welding the fibers together along opposite sides of the rib in the manner described above in connection with the ribs 172.

Figure 3D:
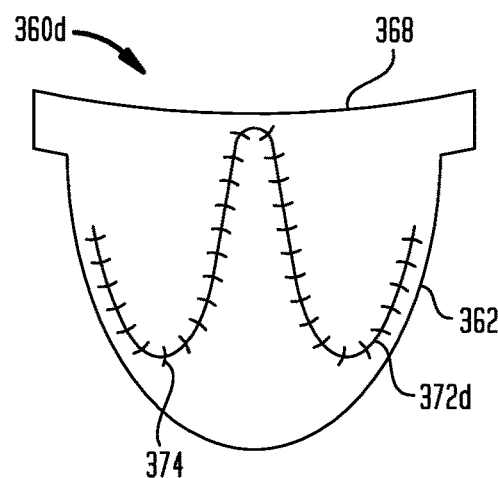

The leaflet 360d shown in FIG. 3D is also similar to the leaflet 360, except that the leaflet 360d includes a single rib 372d that has a serpentine shape with ends adjacent to the belly 362 at opposite ends of the belly, and a central portion that extends across the middle of the leaflet to reach a location adjacent to the center of the free edge 368 of the leaflet. The serpentine shape of the rib 372d may exhibit an improvement in balanced coaptation over the rib 372. The rib 372d may be sutured to a surface of the primary leaflet material by sutures 374. Alternatively, the rib 372d may be attached to the surface of the leaflet 360d by heat sealing or welding fabric strips across the rib to the leaflet 360d in the manner described above in connection with ribs 172. In still a further arrangement, rib 372d may be heat sealed or welded directly to the leaflet when the materials of the leaflet and rib allow for such procedure.

Figure 3E:
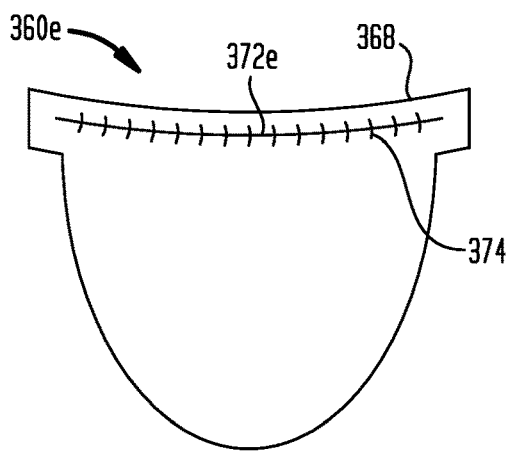

The leaflet 360e shown in FIG. 3E is similar to the leaflet 360d, except that the leaflet 360e includes a single rib 372e that extends along the free edge 368 of the leaflet. The location of the rib 372e adjacent to the free edge 368 may result in an improvement in balanced coaptation over the rib 372, and this location may help prevent the free edge from fluttering and may help limit the range of motion of the free edge to prevent contact with the struts 40 of the stent 12. The rib 372e may be sutured to a surface of the primary leaflet material by sutures 374 or may be threaded or woven through the primary leaflet material. The rib 372e may be secured in place on the leaflet 360e by heat sealing or welding the fibers of the leaflet material on opposite sides of the rib. The rib 372e may also be joined to the leaflet 360e by heat sealing or welding strips of fabric across the rib as described above in connection with ribs 172. Still further, when the materials of the leaflet and rib allow, the rib may be heat sealed or welded directly to the leaflet.

Figure 3F:
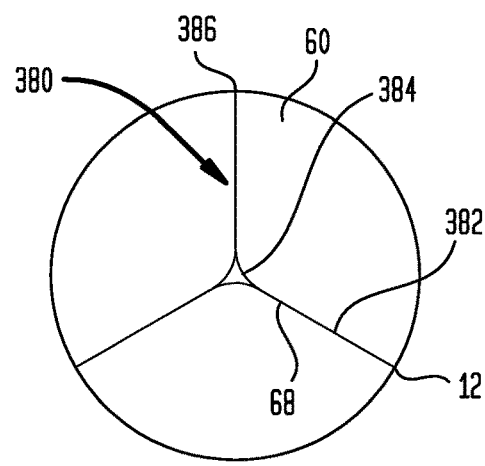
FIG. 3F is a plan view of a fixed support configured for use with the collapsible prosthetic heart valve of FIG. 1.

FIG. 3F illustrates a fixed support 380 having three struts 382 that may be added to the prosthetic heart valve 10 by suspending it in a central opening of the prosthetic heart valve 10 at a location where the leaflets 60 coapt. The struts 382 may be made of a thin wire of nitinol, an MP35 nickel-based alloy, a spring metal, stainless steel, cobalt, or any of the other materials mentioned above with respect to the leaflet 160. The struts 382 may have first ends 384 coupled to one another at a central location within the central opening of the prosthetic heart valve 10 and second ends 386 attached to the stent 12 and/or the cuff 50 of FIG. 1. The fixed support 380 may be configured so that the free edges 68 of the leaflets 60 coapt against it, and the location of the fixed support may assist the leaflets 60 to exhibit more balanced coaptation.

FIGS. 4A-4C illustrate a leaflet 460 according to an embodiment of the invention that may replace each of the leaflets 60 described above with reference to the prosthetic heart valve 10. The leaflet 460 is another variation of the leaflet 160 described above. The leaflet 460 may be similar to the leaflet 160, except that the ribs 472 of its internal skeleton 470 are disposed between two leaflet layers 461a, 461b rather than extending within the primary leaflet material.

In the embodiment shown, leaflet layers 461a and 461b may be two portions of a single sheet of leaflet material (FIG. 4B) that are folded over one another (FIG. 4C) and then fixed together (FIG. 4A) to enclose the ribs 472. Sutures 474 may be used to stitch the two leaflet layers 461a, 461b together. The application of the sutures 474 may be done at the same time as the attachment of the leaflet 460 to the stent 12 and/or the cuff 50 of the prosthetic heart valve 10. Alternatively, leaflet layers 461a, 461b may be joined by adhesive, heat lamination, ultrasonic welding, or other known joining techniques. To ensure the ribs 472 do not move between the layers of leaflet material, each of these joining techniques, including suturing, should be performed adjacent opposite sides of each rib, as well as at other locations at which the layers may be joined together.

In other examples, the leaflet layers 461a and 461b may be separate elements that are laminated, glued, sutured or otherwise joined to one another on opposite sides of the internal skeleton. Any of various biocompatible materials may be used for the leaflet layers 461a, 461b, such as pericardium tissue, polyurethane sheets, fabric, and the like.

The concept of sandwiching the ribs 472 of the internal skeleton 470 between two leaflet layers 461a, 461b may be applied to any configuration of ribs that is disclosed herein. Specifically, the internal skeleton 470 may be replaced with the internal skeleton 170 of FIGS. 2A-2C, the internal skeleton 170' of FIG. 2D, the internal skeleton 370 of FIGS. 3A and 3B, or the variations of the rib geometries shown in FIGS. 3C-3E.

FIG. 5 illustrates a leaflet 560 according to an embodiment of the invention that may replace each of the leaflets 60 described above with reference to the prosthetic heart valve 10. The leaflet 560 may be similar to the leaflet 60, except that the leaflet 560 has a reinforcement 570 disposed at the free edge 568. For example, the primary leaflet material of the leaflet 560 may be pericardial tissue, and the reinforcement 570 may be a strip-shaped sheet of material (e.g., a metal such as nitinol or a semi-rigid polymer) that is applied to one or both of the external surfaces of the primary leaflet material adjacent the free edge 568. The reinforcement 570 may reinforce the primary leaflet material of the leaflet 560 at the coaptation zone to reduce the bending stress at the free edge 568 during leaflet coaptation. The reinforcement 570 may be attached to one or both external surfaces of the primary leaflet material using an adhesive, for example, or other joining techniques including heat lamination and ultrasonic welding. The reinforcement 570 may include a material having properties that are different from those of the primary leaflet material, such as a higher durometer than a durometer of the primary leaflet material, but not so high as to interfere with coaptation.

FIG. 6 illustrates a portion of a leaflet 660 according to an embodiment of the invention that may replace each of the leaflets 60 described above with reference to the prosthetic heart valve 10. The leaflet 660 may be similar to the leaflet 60, except that the leaflet 660 has a reinforcement 670 attached to a part of the belly 662 of the leaflet, at a location at which the leaflet is closest to the stent 12 and/or the cuff 50 of the prosthetic heart valve 10. The reinforcement 670 may comprise a material having properties that are different from those of the primary leaflet material, such as a higher elasticity than the primary leaflet material, so that strain within the primary leaflet material may be reduced. The reinforcement 670 may comprise reinforced silicones, urethanes, or a fabric such as Dacron, among other materials. The reinforcement 670 may include a material having other properties different from those of the primary leaflet material, such as a higher durometer than a durometer of the primary leaflet material, but not so high as to interfere with coaptation.

The reinforcement 670 may extend along an edge of the belly 662 of the leaflet 660, with a portion of the reinforcement attached to the leaflet. The remainder of the reinforcement 670 may extend beyond the edge of the belly 662 of the leaflet 660, so only the material of the reinforcement is directly attached to the stent 12 and/or the cuff 50. In other examples (not shown), the reinforcement 670 may not extend beyond the edge of the belly 662 of the leaflet 660, so that there may be direct contact between the primary leaflet material and the stent 12 and/or the cuff 50. The reinforcement may be attached to the material of the leaflet by any of the techniques noted previously, including adhesive, heat lamination, ultrasonic welding or suturing. Regarding the attachment of the leaflet 660 to the stent 12 and/or the cuff 50, there are a few ways that the reinforcement 670 and the edge of the belly 662 can be arranged. In one, example the reinforcement 670 may lie on top of the leaflet 660 and sutures may extend through the leaflet and the reinforcement to attach the leaflet to the stent 12 and/or the cuff 50. In another example, the reinforcement 670 may wrap around the edge of the belly 662 so that one portion is on top of the leaflet and another portion is on the bottom of the leaflet, and sutures may extend though both the leaflet and the two portions of the reinforcement for attachment to the stent 12 and/or the cuff 50. Alternatively, the sutures may extend only through the two portions of the reinforcement 670 for attachment to the stent 12 and/or the cuff 50 without extending though the belly 662 of the leaflet 660.

Figure 7A:
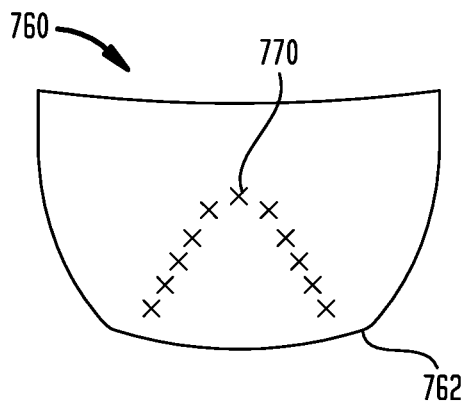
FIG. 7A is a plan view of another embodiment of a leaflet suitable for use with the collapsible prosthetic heart valve of FIG. 1.
Figure 7B:
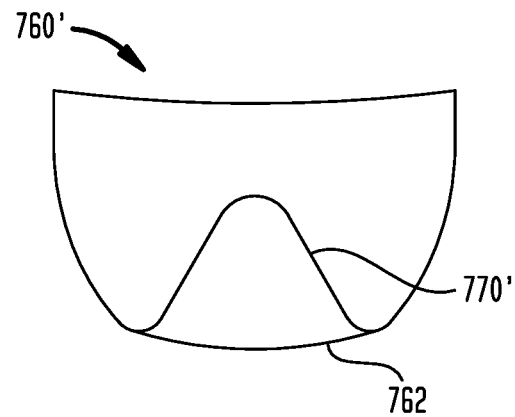
FIG. 7B is a plan view of a leaflet that is a variation of the leaflet of FIG. 7A.

FIGS. 7A and 7B illustrate leaflets 760 and 760' according to embodiments of the invention that may replace each of the leaflets 60 described above with reference to the prosthetic heart valve 10. The leaflet 760 may be similar to the leaflet 60, except that the leaflet 760 includes reinforcements 770 in the form of sutures or other stitches in a central region of the leaflet extending towards the belly 762. The reinforcements 770 may provide a surface feature that is more resistant to abrasion than the primary leaflet material. As shown in FIG. 7A, the reinforcements 770 may form an inverted U or V shape extending from a central region of the leaflet towards the belly 762. However, in other examples, the specific shape or pattern of the reinforcements 770 may be adjusted to provide reinforcement in regions of the leaflet 760 that are most susceptible to abrasion. The reinforcements 770 (e.g., the sutures or other stitches) may include a material having a higher durometer than a durometer of the primary leaflet material, but not so high as to interfere with coaptation, or other properties that are different from those of the primary leaflet material.

The leaflet 760' shown in FIG. 7B is a variation of the leaflet 760 that may be similar to the leaflet 60, except that the leaflet 760' includes a reinforcement 770' in the form of a fabric attached to a surface of the primary leaflet material in a central region of the leaflet extending towards the belly 762. The reinforcement 770' may be an ultra-thin low density fabric or a similar material that is more resistant to abrasion than the primary leaflet material. As shown in FIG. 7B, the reinforcement 770' may have an inverted U or V shape extending from a central region of the leaflet towards the belly 762. However, in other examples, the specific shape of the reinforcement 770' may be adjusted to provide reinforcement in regions of the leaflet 760' that are most susceptible to abrasion. The reinforcement 770' may include a material having certain properties that are different from the properties of the primary leaflet material. For example, the reinforcement may have a higher durometer than a durometer of the primary leaflet material, but not so high as to interfere with coaptation. The reinforcement 770' may attached to the leaflet 760' by heat lamination, ultrasonic welding, suturing or other known techniques.

Figure 8A:
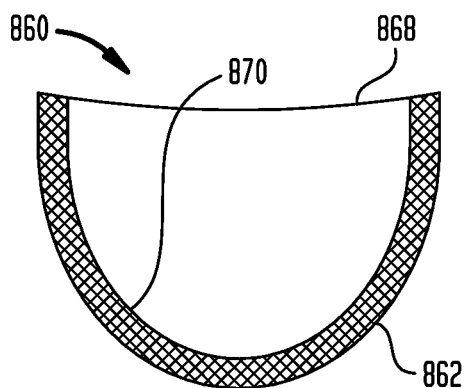
FIG. 8A is a plan view of another embodiment of a leaflet suitable for use with the collapsible prosthetic heart valve of FIG. 1.
Figure 8B:
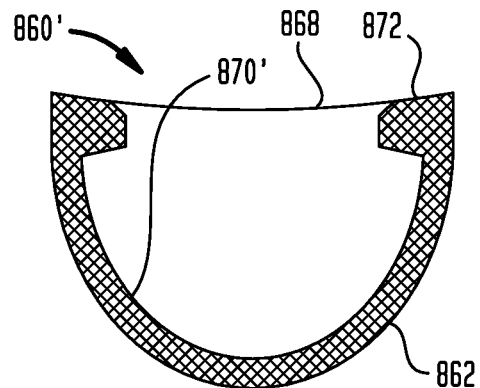
FIG. 8B is a plan view of a leaflet that is a variation of the leaflet of FIG. 8A.

FIGS. 8A and 8B illustrate leaflets 860 and 860' according to embodiments of the invention that may replace each of the leaflets 60 described above with reference to the prosthetic heart valve 10. The leaflet 860 may be similar to the leaflet 60, except that the leaflet 860 includes a reinforcement 870 attached to a surface of the primary leaflet material extending across the belly 862 of the leaflet, at locations at which the leaflet may be sewn to the stent 12 and/or the cuff 50 of the prosthetic heart valve 10. The reinforcement 870 may provide additional strength and suture retention support in addition to the primary leaflet material. The reinforcement 870 may include a material having a higher durometer than a durometer of the primary leaflet material, but not so high as to interfere with coaptation, or may have other material properties that are different from those of the primary leaflet material. As shown in FIG. 8A, the reinforcement has a shape that conforms to the edge contour of the belly 862 of the leaflet. However, in other examples, the specific shape of the reinforcement 870 may be adjusted to provide reinforcement in any other regions of the leaflet 860. The reinforcement 870 may comprise a material such as fabric, tissue, or one or more polymers.

The leaflet 860' shown in FIG. 8B is similar to the leaflet 860, except that the reinforcement 870' is wider at two corner locations 872 at which the belly 862 meets the free edge 868. The corner locations 872 are the locations of the leaflet 860' that are stitched to the commissure attachment features 44 of the stent 12 of the prosthetic heart valve 10, so the leaflet 860' may provide additional strength and suture retention support at these high-stress locations.

Figure 8C:
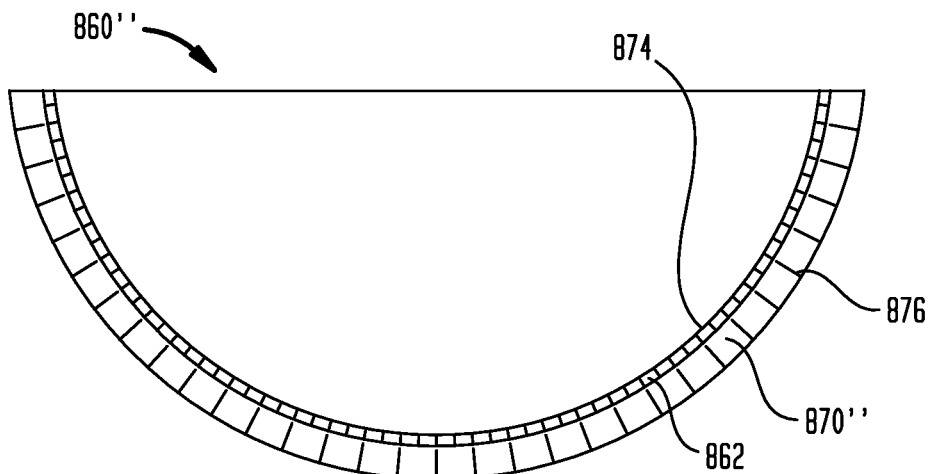
FIG. 8C is a plan view of a leaflet that is another variation of the leaflet of FIG. 8A.

The leaflet 860" shown in FIG. 8C is also similar to the leaflet 860, except that the reinforcement 870" extends beyond the edge of the belly 862. The inner edge 874 of the reinforcement 870" overlaps with the primary leaflet material for the part of the reinforcement 870" that is radially inside of the edge of the belly 862. The outer edge 876 of the reinforcement 870" extends beyond the edge of the belly 862, such that there is no overlap with the primary leaflet material for the part of the reinforcement 870" that is radially outside of the edge of the belly. In this variation, only the reinforcement 870" and not the primary leaflet material is directly stitched to the stent 12 and/or the cuff 50, so that the reinforcement 870" bears a higher portion of the stress at the attachment points to the stent and/or the cuff. The reinforcement 870" may be stronger than the primary leaflet material, so that permitting stress from the attachment of the leaflet 860" to the stent 12 and/or the cuff 50 to be borne by the reinforcement may improve the durability of the primary leaflet material.

For any of the leaflets 860, 860', and 860", various methods may be used to attach the reinforcement 870, 870', or 870" to the primary leaflet material. In one example, a single reinforcement 870, 870', or 870" may be sewn, glued, heat sealed or otherwise attached to a single surface of the primary leaflet material at or adjacent to the edge of the belly 862. In another example, two separate reinforcements 870, 870', or 870" may be sewn, glued, heat sealed or otherwise attached to both the top and bottom surfaces of the primary leaflet material at or adjacent to the edge of the belly 862. In yet another example, a single reinforcement 870, 870', or 870" may be sewn, glued, heat sealed or otherwise attached between two adjacent layers of primary leaflet material at or adjacent to the edge of the belly 862.

Figure 9A:
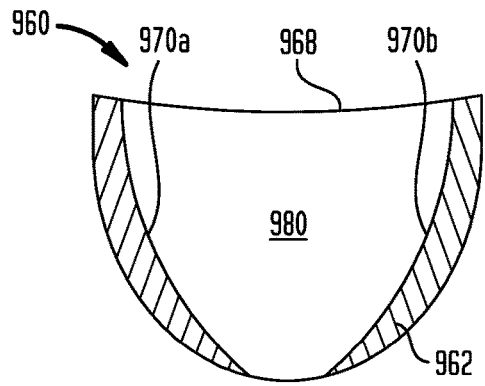
FIG. 9A is a plan view of another embodiment of a leaflet suitable for use with the collapsible prosthetic heart valve of FIG. 1.
Figure 9B:
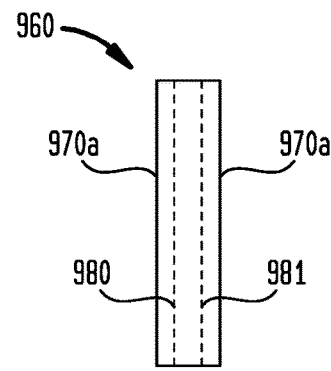
FIG. 9B is a side view of the leaflet of FIG. 9A.

The leaflet 960 shown in FIGS. 9A and 9B is a variant that is similar to the leaflet 860, except that the leaflet 960 has two reinforcements 970a, 970b that extend from a central part of the belly 962 to opposite ends of the free edge 968, with the width of each reinforcement narrowing in a direction from the free edge towards the central part of the belly. The reinforcements 970a, 970b each may comprise a material such as fabric, tissue, or one or more polymers. The reinforcements 970a, 970b may include a material having properties that are different from those of the primary leaflet material, such as a higher durometer than a durometer of the primary leaflet material, but not so high as to interfere with coaptation.

As can be seen in FIG. 9B, the reinforcement 970a is attached to both opposite surfaces of the primary leaflet material. A single reinforcement 970a and a single reinforcement 970b may each wrap around a portion of the edge of the belly 962 of the leaflet 960, or two separate reinforcements 970a and two separate reinforcements 970b may be attached on respective top and bottom surfaces 980, 981 of the primary leaflet material at or adjacent respective portions of the belly 962. Any of the attachment techniques discussed above may be used, including adhesive, heat sealing or lamination, ultrasonic welding or suturing, as well as any other known technique.

Figure 10A:
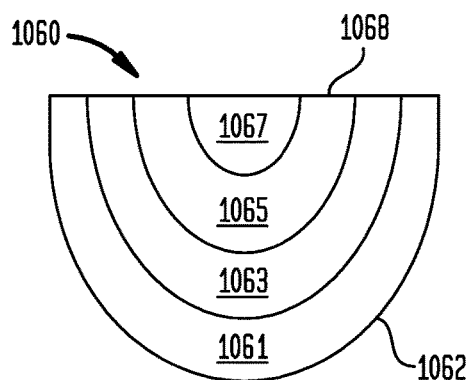
FIG. 10A is a plan view of another embodiment of a leaflet suitable for use with the collapsible prosthetic heart valve of FIG. 1.
Figure 10B:
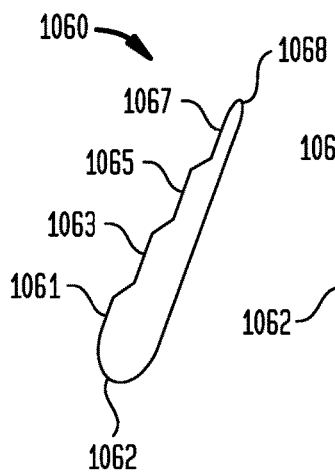
FIG. 10B is a side view of the leaflet of FIG. 10A.
Figure 10C:
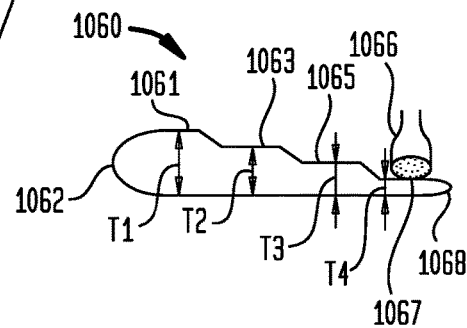
FIG. 10C is a side view of the leaflet of FIG. 10A, shown with a shaver.

FIGS. 10A-10C illustrate a leaflet 1060 according to an embodiment of the invention that may replace each of the leaflets 60 described above with reference to the prosthetic heart valve 10. The leaflet 1060 may be similar to the leaflet 60, except that the leaflet 1060 has first, second, third, and fourth regions 1061, 1063, 1065, and 1067 that have increasingly smaller respective thicknesses T1, T2, T3, and T4, as the distance from the edge of the belly 1062 increases. The difference between the greatest thickness T1 and the smallest thickness T4 is greater than 0.0015", which is not possible through normal variation of pericardium tissue thickness, which is typically used for tissue leaflets of prosthetic valves.

The leaflet 1060 is thickest in the first region 1061 at the belly 1062, which is the area of attachment to the stent 12 and/or the cuff 50, and the leaflet gets progressively thinner moving away from the belly and towards the center of the free edge 1068. As shown in FIGS. 10A-10C, the cross-section of the leaflet 1060 has a thickness that steps down at the transition between each successive region 1061-1067.

The inventors have found that FEA analysis suggests that the highest stresses on conventional leaflets occurs near the belly of the leaflets, where the leaflet is attached to the stent and/or cuff. Altering the thickness of the leaflet 1060 such that it is thicker in the area of highest stresses near the belly 1062 may permit the leaflet to better withstand stresses in that portion of the leaflet compared to conventional leaflet designs.

If the entire leaflet 1060 was to have a sufficient thickness to more easily accommodate or withstand the stresses near the belly 1062, then it may not be possible to sufficiently compress the prosthetic heart valve having the leaflets 1060 into a conventional delivery device for transfemoral delivery to a native annulus in a patient. Reducing the thickness of the leaflet 1060 from the belly 1062 towards the center of the free edge 1068 compared to a conventional tissue leaflet may provide a durability advantage for the leaflet at locations at which the stress is greatest, while reducing the collapsed volume of the leaflet by removing volume from areas of the leaflet where the stress is lower.

One exemplary method of forming the leaflet 1060 having regions 1061-1067 with thicknesses T1-T4 is to mechanically remove tissue material using a shaver, blade or laser to create the different thicknesses. In the example shown in FIG. 10C, a shaver 1066 having a small circular shaver head may be used to sculpt leaflet tissue having an initial thickness of at least T1, shaving away different amounts of material in different regions, so that the regions 1061-1067 will have the desired thicknesses T1-T4.

In another example, a chemical etching process may be used to reduce the thickness of each of the regions 1061-1067 to create the different thicknesses T1-T4. A mold may be placed over the initial leaflet tissue such that a chemical (e.g., acid or collagenase enzyme) could be selectively applied to each of the regions 1061-1067. The amount of tissue removed could be controlled by the length of time the tissue is exposed to the chemical or the concentration of the chemical, with the highest time of exposure or the highest concentration of etching chemical being in region 1067 where the greatest thickness reduction is needed.

Figure 10D:
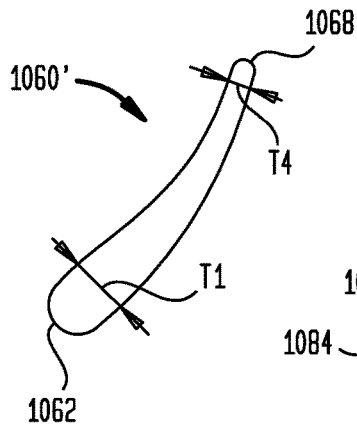
FIG. 10D is a side view of a leaflet that is a variation of the leaflet of FIG. 10A.

FIG. 10D illustrates a leaflet 1060' according to a variant that is similar to the leaflet 1060, except that the leaflet 1060' has a continuously varying thickness starting at T1 near the belly 1062 and decreasing to T4 as the distance from the edge of the belly increases to a maximum, which is at a center of the free edge 1068.

Figure 10E:
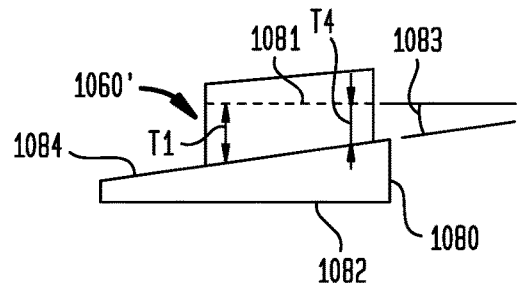
FIG. 10E is a side view of an in-process stage of producing the leaflet of FIG. 10D.

FIG. 10E illustrates a process that may be used to reduce the thickness of portions of the leaflet 1060' in a continuously varying manner. An initial tissue leaflet may be placed on an angled plate 1080, and a flat blade or a laser may be used to produce a straight cut line 1081 that is substantially parallel to a bottom surface 1082 of the angled plate but that is at an angle 1083 to a top surface 1084 of the angled plate.

Figure 10F:
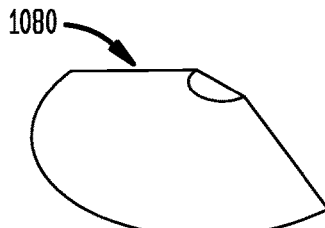
FIG. 10F is a perspective view of the angled plate of FIG. 10E.

As can be seen in FIG. 10F, the angled plate 1080 would have a varied thickness in two dimensions, so that the resulting thickness of the leaflet 1060' would vary somewhat similarly to the thickness of the leaflet 1060, but in a continuously variable manner rather than in a stepwise manner. The straight cut line 1081 would remove more material near the center of the free edge 1068 than near the belly 1062. The resulting thickness would be T1 near the belly 1062 and T4 at a center of the free edge.

Figure 11A:
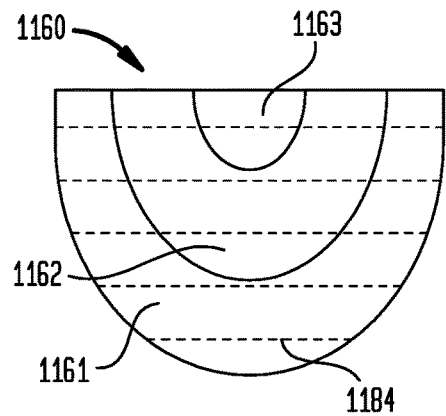
FIG. 11A is a plan view of a leaflet that is another variation of the leaflet of FIG. 10A.

FIG. 11A illustrates a leaflet 1160 according to a variant that is similar to the leaflet 1060, except that the leaflet 1160 is formed through an additive process to produce first, second, and third regions 1161-1163 with thicknesses T1-T3, rather than the subtractive processes described with reference to FIGS. 10C and 10E.

Figure 11B:
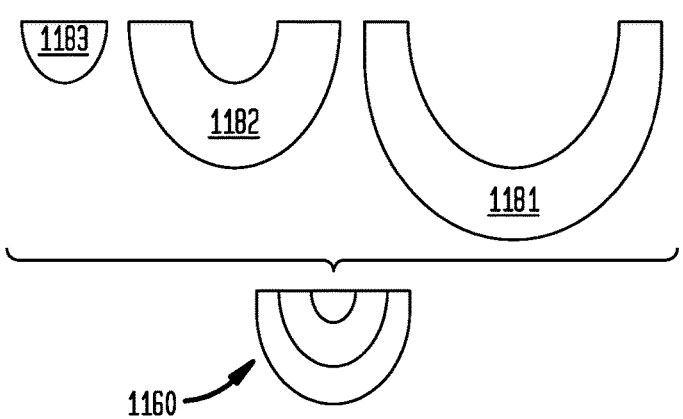
FIG. 11B is a plan view of an in-process stage of making the leaflet of FIG. 11A.

As shown in FIG. 11B, formation of the leaflet 1160 may begin with thin tissue layers 1181, 1182, and 1183 of different surface areas but all with the same thickness T3, and the thin tissue layers may be vertically stacked so that the thinnest region 1163 has the thickness T3 of a single layer 1183, the middle region 1162 has a combined thickness T2 of two stacked layers 1182 and 1183, and the thickest region 1161 has a combined thickness T1 of three stacked layers 1181-1183.

The layers 1181-1183 could be stitched together with sutures 1184 as shown in FIG. 11A, or alternatively, the tissue could be glued together with a fibrin glue, or stacked together and incubated with growth medium such that the cells present in the pericardium create collagen fibers to fuse the tissue together. If the cells already present in the pericardium are not sufficient to fuse the tissue, external cells such as fibroblasts could be seeded onto the tissue surfaces to be fused prior to incubation.

Figure 11C:
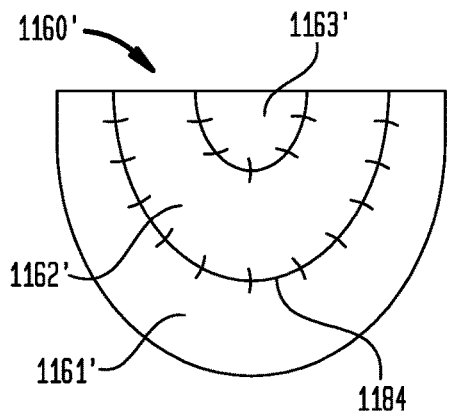
FIG. 11C is a plan view of a leaflet that is a variation of the leaflet of FIG. 11A.

FIG. 11C illustrates a leaflet 1160' according to a variant that is similar to the leaflet 1160, except that the leaflet 1160' is formed through an additive process to produce first, second, and third regions 1161'-1163' with thicknesses T1-T3 by using tissue layers 1181'-1183' having different thicknesses, rather than the same thickness.

Figure 11D:
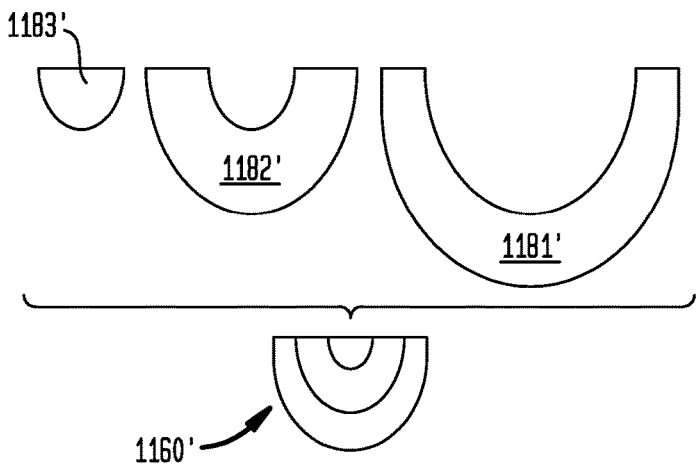
FIG. 11D is a plan view of an in-process stage of making the leaflet of FIG. 11C.

As shown in FIG. 11D, formation of the leaflet 1160' may begin with initial tissue layers 1181'-1183' of different surface areas and different thicknesses T1-T3, and the tissue layers may be laterally joined so that the final regions 1161'-1163' have the same thicknesses as the respective initial tissue layers 1181'-1183'. The layers 1181'-1183' could be stitched together with sutures 1184 as shown in FIG. 11C, or alternatively, the tissue could be glued together with a fibrin glue, or fused together as described above with reference to FIG. 11B. In this variant, the layers 1181'-1183' nest in one another, such that the convex outer contour of the layer 1182' nests into the concave inner contour of the layer 1181', and the convex outer contour of the layer 1183' nests into the concave inner contour of the layer 1182'.

Figure 12:
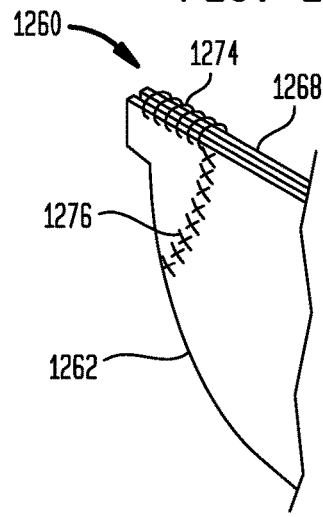
FIG. 12 is a perspective view of a pair of leaflets suitable for use with the collapsible prosthetic heart valve of FIG. 1.

FIG. 12 illustrates leaflets 1260 according to an embodiment of the invention that may replace the leaflets 60 described above with reference to the prosthetic heart valve 10. The leaflet 1260 may be similar to the leaflet 60, except that the leaflets 1260 are coupled together via the sutures 1274 and/or the sutures 1276. The sutures 1274 and/or the sutures 1276 couple adjacent ones of the leaflets together such that when one starts to move, the other one also moves. Such coupling of the leaflets 1260 to one another may structurally reinforce the sutured region of the leaflets and may improve the balance of coaptation (i.e., all three leaflets coapting at the same time).

The sutures 1274 are disposed at the free edges 1268 of adjacent ones of the leaflets 1260 at the ends of the free edges adjacent the attachment to the commissure attachment features 44. The sutures 1276 extend in an arc from the free edges 1268 of adjacent ones of the leaflets to the bellies 1262 of adjacent ones of the leaflets. Either one or both of the sutures 1274 and the sutures 1276 may be implemented in a single prosthetic heart valve, depending on the degree of coupling between the leaflets 1260 that is desired. Although sutures 1274 and 1276 are shown in FIG. 12, in other examples, alternative mechanisms may be used to couple the leaflets 1260 to one another, such as a clip or staples made of a metal or a polymer.

The incorporation of any of the reinforcements described above may enable the prosthetic heart valve to provide visualization advantages during the deployment of the heart valve within a patient. During deployment, radiologic imaging, such as fluoroscopy, is often used to visualize the prosthetic heart valve and assure its proper positioning in the native valve annulus. Accurate positioning of the prosthetic heart valve is important in ensuring the prosthetic device functions properly. However, since many of the materials from which the prosthetic valves are formed are not radiopaque, such imaging is of limited help in accurately positioning the heart valve at the proper depth and rotational orientation in the native valve annulus.

In any of the embodiments described above, the internal skeleton or other reinforcement may be formed from a biocompatible material that is highly radiopaque, such as gold, tantalum, platinum, iridium, barium, tungsten, or any combination thereof, or any other biocompatible materials used for their radiographic properties in medical devices. For example, internal skeletons 170, 170', 370 and 470 (including ribs 172, 172', 372, 372*c*, 372*d*, 372*e* and 472), and reinforcement 570 may be formed from a highly radiopaque material. In addition, the sutures forming reinforcements 770 and 770' may be formed from a highly radiopaque material. The radiopacity of these materials is significantly greater than the radiopacity of the primary leaflet material such that, when visualized under radiographic imaging, these reinforcing structures will be readily visible, identifying the rotational positions of the leaflets relative to the native valve structures, such as the native leaflet commissures. As such, it will be possible to rotate the prosthetic valve relative to the native valve structures to ensure the prosthetic valve is in the optimum position prior to its full deployment.

It will be appreciated that some of the reinforcements described above may be formed of fabric, tissue or polymers that are not inherently highly radiopaque. Although it may be possible to replace those materials with materials that are radiopaque, or to incorporate a radiopaque material in the fabric, tissue or polymer, or in regions thereof, as desired, that may not be always possible. At other times, each of the valve leaflets may have the same radiopaque internal skeleton or other reinforcing structure, such that the leaflets will be visible under radiographic imaging, but it will not be possible to discern one leaflet from another. In both of these situations, it may be possible to incorporate one or more radiopaque markers in all of the leaflets of the prosthetic valve, or less than all of the leaflets, as desired. Any such markers may be formed from the same materials as noted above, and may be formed in any geometric shape, including round, oval, rectangular, triangular, trapezoidal and the like, as well as in non-geometric shapes, including numbers, letters, arrows, or any other useful shape. All of the leaflets of a single prosthetic valve may have markers with the same shape and positions, or one or more leaflets may have markers with a shape and/or position that is different from those of the other leaflets. Additionally, where a leaflet has more than one marker, all of the markers on the leaflet may have the same shape or some or all of the markers on a leaflet may have different shapes.

The markers may be placed at those positions on the prosthetic heart valve leaflets it is desirable to identify or visualize during deployment of the prosthetic heart valve in a patient or possibly after the heart valve has been functioning in the patient for a period of time. For example, markers may be placed on the leaflets at positions at or adjacent the leaflet commissures to facilitate the accurate rotational orientation and positioning of the prosthetic heart valve relative to the native valve commissures and leaflets. As another example, markers may be placed at one or more locations along the free edge of each leaflet. When viewed under radiographic imaging, these markers may make it possible to visualize whether the leaflets are opening, closing and coapting properly during operation of the prosthetic heart valve. These markers may also make it possible to more readily discern using radiographic imaging that the prosthetic heart valve continues to operate properly after a period of time following implantation in a patient.

Although the invention herein has been described with reference to collapsible and/or expandable prosthetic heart valve embodiments, it is to be understood that the stress-reducing leaflet features described herein (e.g., the internal skeletons and the reinforcements) may also be applied to leaflets of mechanical heart valves. Exemplary mechanical heart valves to which the features described herein may be applied are described in the U.S. provisional patent application 62/902,044, the disclosure of which is hereby incorporated by reference herein.

In summary, the disclosure herein describes multiple embodiments of a prosthetic heart valve including an expandable stent having an inflow end, an outflow end, an annulus section adjacent the inflow end, and a plurality of cells connected to one another in a plurality of annular rows around the stent; a cuff attached to the annulus section of the stent; a plurality of leaflets disposed within an interior region of the stent and attached to at least one of the cuff or the stent, the leaflets together having a coapted position occluding the interior region of the stent and an open position in which the interior region is not occluded, each of the leaflets including a primary leaflet material; and a reinforcement attached to the primary leaflet material of each of the leaflets, the reinforcement including a material having properties that are different from properties of the primary leaflet material; and/or the reinforcement may include a plurality of ribs that are spaced apart from one another in a direction that is parallel to an outer surface of a respective one of the leaflets; and/or each of the ribs may be disposed in an interior volume of the leaflet and may include an extension that extends out from the interior volume of the leaflet, and the extensions may be coupled to commissure attachment features of the stent; and/or each of the ribs may be formed from the primary leaflet material; and/or the reinforcement may include a single curved rib having a shape that matches a contour of a belly of a respective one of the leaflets; and/or the reinforcement may include a single rib that extends along a free edge of a respective one of the leaflets; and/or the reinforcement may extend between two leaflet layers that overlie one another on opposite sides of the reinforcement, the two leaflet layers being fixed to one another; and/or the primary leaflet material may have a first radiopacity and the reinforcement may be formed from a material having a second radiopacity greater than the first radiopacity; and/or the reinforcement may be attached to an outer surface of the primary leaflet material of each of the leaflets; and/or the reinforcement may include a single strip-shaped sheet of material that extends along a free edge of the leaflet; and/or the reinforcement may include a sheet of fabric extending from a portion of a belly of the leaflet towards a central region of the leaflet; and/or each of the leaflets may include a belly having a curved edge, and the reinforcement may include a curved strip of material extending along the curved edge of the belly and having a shape that matches the curved edge of the belly; and/or the curved strip of material may include a first portion that overlies the curved edge of the belly and a second portion that extends outwardly beyond the curved edge of the belly, the second portion of the curved strip of material being directly attached to the stent or the cuff; and/or the reinforcement may include two spaced-apart strips of material each extending along a respective portion of the curved edge of a belly; and/or the reinforcement may include a material having a higher durometer than a durometer of the primary leaflet material.

Also described herein are multiple embodiments of a prosthetic heart valve including an expandable stent having an inflow end, an outflow end, an annulus section adjacent the inflow end, and a plurality of cells connected to one another in a plurality of annular rows around the stent; a cuff attached to the annulus section of the stent; a plurality of leaflets disposed within an interior region of the stent and attached to at least one of the cuff or the stent, the leaflets together having a coapted position occluding the interior region of the stent and an open position in which the interior region is not occluded, each of the leaflets including as primary leaflet material; and a reinforcement attached to the primary leaflet material of each of the leaflets, the reinforcement including a series of sutures exposed in a central region of an outer surface of the leaflet.

Further described herein are multiple embodiments of a prosthetic heart valve including an expandable stent having an inflow end, an outflow end, an annulus section adjacent the inflow end, and a plurality of cells connected to one another in a plurality of annular rows around the stent; a cuff attached to the annulus section of the stent; a plurality of leaflets disposed within an interior region of the stent and attached to at least one of the cuff or the stent, the leaflets together having a coapted position occluding the interior region of the stent and an open position in which the interior region is not occluded, each of the leaflets including a primary leaflet material, and each of the leaflets having a thickness that varies from a belly edge of the leaflet to a free edge of the leaflet; and/or each of the leaflets may have an outer surface and a plurality of regions adjacent to one another in lateral directions parallel to the outer surface, a first one of the regions adjacent the belly edge having a first constant thickness and a second one of the regions adjacent the free edge having a second constant thickness less than the first constant thickness; and/or the first one of the regions may be formed from first and second layers of the primary leaflet material, the first layer may be stacked atop the second layer so that the first and second layers together have the first constant thickness, and the second one of the regions may be formed from the second layer that has the second constant thickness; and/or the first one of the regions may be formed from a first layer of the primary leaflet material that has the first constant thickness, and the second one of the regions may be formed from a second layer of the primary leaflet material that has the second constant thickness, and the first and second layers may be disposed adjacent to one another in the lateral directions; and/or the thickness of each of the leaflets may smoothly transition from a first thickness at the belly edge of the leaflet to a second thickness at a center of the free edge of the leaflet, the first thickness being greater than the second thickness; and/or the primary leaflet material may have a first radiopacity and at least one of the leaflets may include a marker having a second radiopacity greater than the first radiopacity.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
   an expandable stent having an inflow end, an outflow end, an annulus section adjacent to the inflow end, and a plurality of cells connected to one another in a plurality of annular rows around the stent;
   a cuff attached to the annulus section of the stent;
   a plurality of leaflets disposed within an interior region of the stent and attached to at least one of the cuff or the stent, the leaflets together having a coapted position occluding the interior region of the stent and an open position in which the interior region is not occluded, each of the leaflets including a primary leaflet material; and
   a reinforcement attached to the primary leaflet material of each of the leaflets, the reinforcement including a material having properties that are different from properties of the primary leaflet material;
   wherein the reinforcement includes a plurality of ribs that are spaced apart from one another in a direction that is parallel to an outer surface of a respective one of the leaflets; and wherein each of the plurality of ribs includes an extension that extends out from the leaflet, the extensions being coupled to commissure attachment features of the stent.

2. The prosthetic heart valve of claim 1, wherein the plurality of ribs are disposed in an interior volume of the leaflet.

3. The prosthetic heart valve of claim 1, wherein the reinforcement extends between two leaflet layers that overlie one another on opposite sides of the reinforcement, the two leaflet layers being fixed to one another.

4. The prosthetic heart valve of claim 1, wherein the primary leaflet material has a first radiopacity and the reinforcement is formed from a material having a second radiopacity greater than the first radiopacity.

5. The prosthetic heart valve of claim 1, wherein the reinforcement is attached to an outer surface of the primary leaflet material of each of the leaflets.

6. The prosthetic heart valve as claimed in claim 1, wherein the reinforcement includes a material having a higher durometer than a durometer of the primary leaflet material.

7. The prosthetic heart valve of claim 1, wherein the plurality of ribs are partially embedded within an interior volume of the leaflet.

8. The prosthetic heart valve of claim 1, wherein the plurality of ribs are woven between fibers of the primary leaflet material.

9. The prosthetic heart valve of claim 1, wherein the plurality of ribs have a roughened outer surface.

10. The prosthetic heart valve of claim 1, wherein the plurality of ribs are spaced out between a free edge of the leaflet and a belly of the leaflet.

11. The prosthetic heart valve of claim 1, wherein the plurality of ribs are bowed to a radius of curvature between that of a free edge of the respective leaflet and a belly of the leaflet.

12. A prosthetic heart valve, comprising:
an expandable stent having an inflow end, an outflow end, an annulus section adjacent the inflow end, and a plurality of cells connected to one another in a plurality of annular rows around the stent;
a cuff attached to the annulus section of the stent; and
a plurality of leaflets disposed within an interior region of the stent and attached to at least one of the cuff or the stent, the leaflets together having a coapted position occluding the interior region of the stent and an open position in which the interior region is not occluded, each of the leaflets including a primary leaflet material, and each of the leaflets having a thickness that varies from a belly edge of the leaflet to a free edge of the leaflet;
wherein each of the leaflets has an outer surface and a plurality of regions adjacent to one another in lateral directions parallel to the outer surface, a first one of the regions adjacent the belly edge having a first constant thickness and a second one of the regions adjacent the free edge having a second constant thickness less than the first constant thickness;
wherein the first one of the regions is formed from first and second layers of the primary leaflet material, the first layer is stacked atop the second layer so that the first and second layers together have the first constant thickness, and the second one of the regions is formed from the second layer that has the second constant thickness.

13. The prosthetic heart valve of claim 12, wherein the primary leaflet material has a first radiopacity and at least one of the leaflets includes a marker having a second radiopacity greater than the first radiopacity.

14. The prosthetic heart valve of claim 12, wherein the primary leaflet material has a first radiopacity and at least one of the leaflets includes a marker having a second radiopacity greater than the first radiopacity.

15. A prosthetic heart valve, comprising:
an expandable stent having an inflow end, an outflow end, an annulus section adjacent the inflow end, and a plurality of cells connected to one another in a plurality of annular rows around the stent;
a cuff attached to the annulus section of the stent; and
a plurality of leaflets disposed within an interior region of the stent and attached to at least one of the cuff or the stent, the leaflets together having a coapted position occluding the interior region of the stent and an open position in which the interior region is not occluded, each of the leaflets including a primary leaflet material, and each of the leaflets having a thickness that varies from a belly edge of the leaflet to a free edge of the leaflet;
wherein each of the leaflets has an outer surface and a plurality of regions adjacent to one another in lateral directions parallel to the outer surface, a first one of the regions adjacent the belly edge having a first constant thickness and a second one of the regions adjacent the free edge having a second constant thickness less than the first constant thickness;
wherein the first one of the regions is formed from a first layer of the primary leaflet material that has the first constant thickness, and the second one of the regions is formed from a second layer of the primary leaflet material that has the second constant thickness, and the first and second layers are disposed adjacent to one another in the lateral directions.

* * * * *